United States Patent
Roberts et al.

(10) Patent No.: US 6,310,223 B1
(45) Date of Patent: Oct. 30, 2001

(54) PROCESS FOR THE MANUFACTURE OF 1,2-EPOXYBUTANE

(75) Inventors: Brian Dale Roberts, South Euclid, OH (US); John Robert Monnier; David Martin Hitch, both of Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/702,109

(22) Filed: Oct. 30, 2000

Related U.S. Application Data

(62) Division of application No. 09/260,115, filed on Mar. 2, 1999, now Pat. No. 6,180,559.

(51) Int. Cl.$^7$ .................................................. C07D 301/03
(52) U.S. Cl. ......................... 549/523; 549/537; 549/513
(58) Field of Search ..................... 502/326, 251, 502/252, 261, 327, 328, 340, 407, 414; 501/104, 133, 135; 423/608, 635, 641; 549/523, 537, 513

(56) References Cited

U.S. PATENT DOCUMENTS

| | | |
|---|---|---|
| 2,561,984 | 7/1951 | Hillyer et al. . |
| 3,336,241 * | 8/1967 | Shokal ...................................... 260/2 |
| 4,166,047 | 8/1979 | Harsono et al. . |
| 4,743,699 * | 5/1988 | Page et al. .............................. 556/23 |
| 4,897,498 | 1/1990 | Monnier et al. . |
| 5,077,418 | 12/1991 | Falling . |
| 5,117,013 | 5/1992 | Falling . |
| 5,171,920 | 12/1992 | Chaumette et al. . |
| 5,334,791 * | 8/1994 | Cavell et al. ........................ 585/277 |
| 5,391,773 * | 2/1995 | Puckette ................................ 549/540 |
| 5,498,584 * | 3/1996 | Puckette ................................ 502/162 |

FOREIGN PATENT DOCUMENTS

| | | |
|---|---|---|
| 195 32 645 A1 | 3/1997 | (DE) . |
| 196 02 710 A1 | 7/1997 | (DE) . |
| 0 452 182 A | 10/1991 | (EP) . |
| 2 372 770 A | 6/1978 | (FR) . |
| WO 93/16971 | 2/1993 | (WO) . |
| WO 95/24401 A2 | 9/1995 | (WO) . |

OTHER PUBLICATIONS

*Catalytic Hydrogenation Over Platinum Metals*, 1967, pp. 478–483, Academic Press, New York.
Berson, J.A., et al., *J. Am. Chem. Soc.*, 1958, pp. 4341–4345, vol. 80.
Tarbell, D.S., et al., *J. Am. Chem. Soc.*, 1961, pp. 3096–3113, vol. 80.
Tanabe, K., *Solid Acids and Bases*, 1970, pp. 1–33, Academic Press, New York.
Brunauer, S., et al., *J. Am. Chem. Soc.*, 1938, pp. 309–319, vol. 60.
Thomas and Thomas, *Introduction to the Principles of Heterogeneous Catalysis*, 1967, pp. 180–240, Academic Press, London.
Barrett, E.P., et al., *J. Am. Chem. Soc.*, 1951, pp. 373–380, vol. 73.
Moore, W.J., *American Scientist*, Jun. 1960, pp. 109–133, vol. 48.
Aizikovich, M.A., Maretina, I.A., and Petrov, A.A., Catalytic Hydrogenation of Vinylethylene Oxides (I. Hydrogenation of Butadiene Oxide), Zh. Obshch. Khim, 28, 3076–3081, 1958.
Aizikovich, M.A. and Petrov, A.A., Catalytic Hydrogenation of Vinylethylene Oxides (II. Hydrogenation of Chloroprene Oxide), Zh. Obshch. Khim, 28, 3082–3086, 1958.

* cited by examiner

*Primary Examiner*—Steven P. Griffin
*Assistant Examiner*—Cam N. Nguyen
(74) *Attorney, Agent, or Firm*—Matthew W. Smith; Harry J. Gwinnell

(57) ABSTRACT

Processes for the selective preparation of 3,4-epoxy-1-butene (EpB) to 1,2-epoxy-butane (butylene oxide-BO) in the presence of the supported catalysts, comprising one or more Group VIII metals deposited on the support materials which have micropores filled with one or more inorganic oxides.

5 Claims, No Drawings

PROCESS FOR THE MANUFACTURE OF 1,2-EPOXYBUTANE

This is a divisional application of application Ser. No. 09/260,115, filed Mar. 2, 1999, U.S. Pat. No. 6,180,559B1 issued Jan. 30, 2001.

This invention pertains to certain novel catalysts and catalyst support materials and processes for the preparation of the catalyst support materials and for the selective hydrogenation of 3,4-epoxy-1-butene (EpB) to 1,2-epoxybutane (butylene oxide—BO). More specifically, this invention pertains to (1) catalyst support materials having micropores filled with one or more inorganic oxides, (2) a process for the preparation of such catalyst support materials, (3) supported catalysts comprising one or more Group VIII metals deposited on the aforesaid support materials and (4) a process for the selective hydrogenation of EpB to BO using a catalyst comprising rhodium deposited of the aforesaid catalyst support materials.

U.S. Pat. No. 4,897,498 describes an efficient process for the preparation of EpB by the selective monoepoxidation of butadiene. Butylene oxide, which is one of many compounds which may be obtained from EpB, is useful in the manufacture of polyethers, alkylene glycols, aminoalkanols, epoxy resins, urethane polyols and nonionic surfactants and as a stabilizer for chlorinated hydrocarbons and fuel additive.

According to Rylander, *Catalytic Hydrogenation Over Platinum Metals*, Academic Press, New York, page 478 (1967), epoxides, with a few exceptions (Berson and Suzuki, *J. Am. Chem. Soc.*, 80, 4341 [1958]), readily undergo hydrogenolysis over platinum metal catalysts and the major product is usually an alcohol or mixture of alcohols resulting from cleavage of a carbon-oxygen bond; other products may arise by cleavage of the carbon-carbon bond and by loss of the oxygen function. The catalytic hydrogenation of EpB to butyraldehyde over palladium and to 1-butanol over Raney nickel is described in U.S. Pat. No. 2,561,984. No mention is made of the use of rhodium catalysts nor the observation of BO formation. The hydrogenation of EpB also has been reported by Russian workers in *Zh. Obshch. Khim.*, 28, 3046 and 3051 (1958). They hydrogenated EpB in methanol or ethanol with platinum, palladium, and Raney nickel catalysts to give 1-butanol. They state that crotyl alcohol was the principal intermediate in the reduction, although butyraldehyde was also observed. Selective double bond hydrogenation was not observed in any example.

Rhodium has been reported (*J. Am. Chem. Soc.*, 83, 3096 [1961]) to be effective for a double bond reduction in the presence of an epoxide group in a fumagillin derivative. In this literature example, however, the epoxide is trisubstituted and less prone to hydrogenolysis due to steric hindrance. Additionally the double bond and epoxide were not conjugated as they are in EpB. By the term "conjugated" is meant that the carbon-carbon double bond and the epoxide group are adjacent, or stated another way, the epoxide oxygen is attached to the allylic carbon atom. The significance of the conjugated system existing in EpB is demonstrated by Raney nickel-catalyzed hydrogenation of EpB and 1,2-epoxy-7-octene under mild conditions of 50° C. and 3.5 bar total pressure. The hydrogenation of EpB gives 40.5% 1,2-epoxybutane and 58.4% 1-butanol whereas the hydrogenation of 1,2-epoxy-7-octene, wherein the double bond and epoxy group are separated by 4 carbon atoms, gives 94.4% 1,2-epoxyoctane.

U.S. Pat. Nos. 5,077,418 and 5,117,013 disclose the preparation of BO by hydrogenating EpB in the presence of a supported rhodium catalyst. Although the supported rhodium catalysts disclosed in the '418 and '013 patents give excellent selectivities to BO, it has been found that the activity of the catalysts decreases substantially when the catalysts are used to hydrogenate EpB over extended periods of time, e.g., hydrogenation periods in excess of 20 hours or greater. This partial but substantial deactivation of the catalysts represents a severe impediment to the use of the supported rhodium catalysts disclosed in the '418 and '013 patents in a commercial (continuous) process.

German Published Patent Application DE 195 32 645 A1 discloses the preparation of BO by catalytic hydrogenation of EpB in the presence of a heterogeneous catalyst comprising one or more catalytically-active elements of Groups 7 to 11 (Cu, Rh, Ru, Co, Ni, Pd and Pt) which are vapor-deposited under vacuum conditions on oxidized, metal mesh supports. Oxidation of the wire mesh support was conducted at 600 to 1100° C. Vacuum deposition of catalytically-active components such as elements of Groups 7 to 11 is very expensive and requires extended periods of time. Furthermore, the catalytically-active component is very inefficiently distributed on the oxidized, wire mesh support which has a very low surface area, e.g. typically 1 square meter per gram ($m^2/g$) as compared to 20 to 100 $m^2/g$ for conventional catalyst supports. These catalysts require very long reaction times for batch processes or very long contact times for continuous operation to achieve acceptable conversions of EpB. Catalysts prepared according to the above-described methodology described in DE 195 32 645 A1 were prepared and used to hydrogenate EpB to BO. At a reaction temperature of 50° C., reaction times of 2 to 8 hours were required to convert EpB to BO in selective yields.

We have discovered that EpB may be selectively hydrogenated at high rates in the presence of certain supported rhodium catalysts whereby the olefinic unsaturation is hydrogenated without significant hydrogenolysis of the conjugated epoxy group to produce BO without substantial loss of activity over extended periods of operation. The rhodium catalysts which exhibit good to excellent catalytic activity over extended periods of operation comprise rhodium deposited on an inert catalyst support material having micropores blocked or filled with an inorganic oxide. The present invention includes a plurality of novel embodiments:

(1) A catalyst support material having or containing micropores blocked or filled with one or more inorganic oxides.

(2) A process for preparing the catalyst support material of embodiment (1) which comprises the steps of (i) contacting a catalyst support material containing micropores with a solution of an inorganic salt and (ii) drying and calcining the material obtained from step (i) under conditions which convert the inorganic salt to an inorganic oxide to block, e.g., cap or fill the micropores of the catalyst support material.

(3) A catalyst comprising a Group VIII metal deposited on the catalyst support material of embodiment (1).

(4) A process for the manufacture of BO which comprises contacting EpB and hydrogen in the presence of a catalyst comprising rhodium metal deposited on the catalyst support material of embodiment (1).

The first embodiment of the present invention comprises a catalyst support material containing micropores blocked or filled with one or more inorganic oxides. These modified catalyst support materials may be obtained from any of the large number of conventional, porous, refractory catalyst carriers or support materials which are essentially inert in the presence of the reactants used and the product or products obtained from the processes in which catalysts prepared from the modified support materials are employed. Such conventional materials may be of natural or synthetic origin and preferably are of a macroporous structure, although even support materials which are considered macroporous always contain a certain and often significant fraction of micropores. These support materials typically have an apparent porosity of greater than 20%. Supports having a siliceous and/or aluminous composition are, in general, preferred.

Specific examples of suitable supports are the aluminum oxides (including the materials sold under the trade name "Alundum"), charcoal, pumice, magnesia, zirconia, kieselguhr, fuller's earth, silicon carbide, porous agglomerates comprising silicon and/or silicon carbide, silica, selected clays, and artificial and natural ceramics. Refractory supports particularly useful in the preparation of catalysts in accordance with this invention comprise materials having low acidity, e.g., those described by Kozo Tanabe, *Solid Adds and Bases*, pp. 1–28, Academic Press, New York, 1970. α-Alumina and, especially, silica are particularly preferred. The unmodified support materials have a specific surface area of about 5 to 100, preferably 7 to 80, and most preferably 10 to 50 square meters per gram ($m^2/g$) as measured by the B.E.T. method and an apparent porosity as measured by conventional mercury or water absorption techniques of from about 25 to about 50% by volume. The B.E.T. method for determining specific surface area is described in detail in Brunauer, S., Emmet, P. H., and Teller, E., J. Am. Chem. Soc., 60, 309–16 (1938). The unmodified support materials useful in the present invention contain micropores which constitute less than about 50%, preferably about 0.5 to 30%, and most preferably about 0.5 to 20%, of the total surface area of the support material. Mesopores and macropores constitute about 50 to 90% of the total surface area of the support material.

As used herein, the term "micropores" means pores less than a particular diameter (commonly expressed in Angstroms), typically less than 50 Å. The unmodified support materials contain micropores (critical diameters of about 25–50 Å), mesopores, and macropores. There are no clear definitions of diameter size ranges for mesopores and macropores. A detailed description of pore analysis and catalyst supports is presented by Thomas and Thomas, *Introduction to the Principles of Heterogeneous Catalysis*, Academic Press, London (1967 pp. 180–240. The size of 25 Å often is used since analytical methods of pore analysis typically use the value of 25 Å in the calculation of cumulative pore volumes and surface areas of micropores to define the physical properties of catalyst supports.

The actual physical form of the catalyst support material is not particularly important. While the form of the support material has little effect on catalyst activity, practical considerations such as ease of heat transfer, mass transfer, pressure drop due to fluid flow restrictions, efficiency of gas-liquid-solid contacting, catalyst durability, and the like make the use of defined shapes such as spheres, pellets, extrudates, rings, saddles, stars and the like preferred. For conventional, commercial, fixed-bed reactors used in continuous, liquid- and vapor-phase processes, e.g., trickle bed hydrogenation processes and fixed-bed, vapor-phase feed processes, the reactors typically are in the form of a plurality of parallel elongated tubes (in a suitable shell) approximately 1 to 2 inches in diameter and 10 to 50 feet long filled with catalyst. In such reactors, it is desirable to employ a support formed into a rounded shape, such as, for example, spheres, pellets, rings, tablets, stars and the like, having diameters of from about 0.1 inch to about 0.8 inch.

The catalyst support materials of the present invention are characterized by the presence therein of micropores which are blocked or filled with one or more inorganic oxides. Examples of the inorganic oxides are metal oxides which have essentially no acidic character such as oxides of the alkali metals, alkaline earth metals and lanthanides. The alkaline earth metal oxides, especially magnesium oxide, are preferred because of their superior hydrolytic stability. At least 25%, preferably at least 75%, of the total micropore volume is blocked by or filled with the inorganic oxides. The catalyst support materials of the present invention may be prepared by the steps of (i) contacting or immersing a catalyst support material containing micropores in a solution of one or more soluble inorganic salts such as, for example, soluble salts of the alkali metals, alkaline earth metals and lanthanides; (ii) drying the solution-impregnated catalyst support material produced in step (i); and (iii) calcining the material produced in step (ii) under conditions which convert the soluble inorganic salt to an insoluble inorganic oxide, thereby blocking (capping and/or filling micropores present in the catalyst support material. Examples of soluble salts include nitrates; hydroxides; carboxylates, e.g., acetates, oxalates, and the like; halides, e.g., chlorides, etc. The liquid component or phase of the solution may be selected from various inert (non-reactive) liquids such as water, alkanols, aliphatic glycols, aliphatic glycol mono- and di-ethers, amines or a mixture of and two or more such liquids. Step (i) of the process typically is carried out by first determining the micropore volume for a given quantity of catalyst support material according to procedures known to those skilled in the art. For example, micropore volume may be determined by using the mathematical analysis of liquid nitrogen condensation and filling of pores of support material. From the volume of liquid nitrogen required to fill pores and the amount of liquid nitrogen released when the pores are emptied, it is possible to calculate both the distribution of pore diameters and the total volume of pores within a particular pore diameter. Thus, this method can be used to calculate the total volume of pores having diameters less than 50 Å. The mathematical procedure is defined as the Barrett, Joyner and Halenda (BTH) method and is fully described by Barrett, E. P., Joyner, L. S., and Halenda, P. P., J. Am. Chem. Soc., 93, 373–380 (1951).

To ensure micropore filling by inorganic salts, the total volume of micropores of a particular sample was calculated using the BJH method. These data were used to prepare an inorganic salt solution, which contained dissolved inorganic salt in an amount calculated to yield a volume of inorganic oxide that would be slightly in excess of the amount required to fill all the micropores upon decomposition of said salt. The volume occupied by dried inorganic, metal salts is equal to the mass of inorganic salt divided by the density of the salt, wherein density is defined as grams of salt per mL of salt. The appropriate amount of inorganic salt may be dissolved in a quantity of liquid, which approximates the total micropore volume of the support material to be treated in step (i). All, or essentially all, of the inorganic salt solution is absorbed by and into the micropores of the catalyst support material employed in step (i). Normally, the amount of inorganic salt employed in step (i) should be limited to the amount necessary to block only the micropores, i.e., significant blocking of the meso- and macro-pores should be avoided. Upon addition of the inorganic salt solution, the filling of the pores is facilitated by capillary action. The capillary wicking action also facilitates the preferential deposition of the inorganic salt into the micropores as the solvent is removed by evaporation. The solvent evaporates from the larger pores first, leaving the salt concentrated in the solution remaining in the smaller pores. This process continues until all of the solvent has been removed, with the result that the salt is preferentially concentrated in the micropores. This process may be enhanced and improved by using the methodology, commonly known to those skilled in the art, as vacuum impregnation. By first evacuating air out of the support to be impregnated in a suitable vessel, the capillary action is not impeded by the presence of air trapped in the micropores.

Step (ii) may be carried out using conventional procedures and equipment. For example, the solution-impregnated catalyst support may be dried by loading it on trays and placing it in a forced air oven. Or, preferably, for commercial operation, by feeding the material to a continuous vibratory screen type drier. The dried material obtained from step (ii) then is calcined to convert the soluble inorganic salt to an insoluble, inorganic oxide. The step (iii) calcination may be performed by heating the material from step (ii) at a temperature of about 200 to 700° C., preferably about 300 to 500° C., while passing a gas over and/or through the catalyst support material. When the soluble inorganic salt is a hydroxide or nitrate, the gas may be an inert (nonreactive) gas such as nitrogen, helium, carbon dioxide, and the like or the gas may contain oxygen. When using other soluble inorganic salts, e.g., carboxylates or halides, the gas should be an molecular oxygen-containing gas such as air, oxygen-enriched air or an inert gas containing molecular oxygen. The duration of the step (iii) calcination can vary depending on the type of soluble inorganic salt employed but typically is in the range of about 30 to 120 minutes.

The novel catalysts provided by our invention comprise one or more Group VIII metals deposited on a catalyst support material containing micropores blocked with one or more inorganic oxides, i.e., the catalyst support material of embodiment (1). The concentration of Group VIII metal on the catalysts can vary substantially depending, for example, on the particular metal employed and/or the particular chemical process in which the catalyst will be utilized. For example, the amount of Group VIII metal present may be in the range of 0.01 to 10 weight percent based on the total weight of the catalyst. However, the Group VIII metal more typically is present in a concentration of about 0.1 to 5 weight percent (same basis). Palladium, platinum, ruthenium, iridium, and, especially, rhodium represent the preferred Group VIII metals.

The novel supported Group VIII metal catalysts may be prepared in a manner analogous to the process used to prepare the pore-blocked catalyst support material. For example, the catalysts may be prepared by the steps comprising (1) contacting (immersing) the catalyst support material of embodiment (i) in a solution of a soluble Group VIII, (2) drying the material from step (1), and (3) reducing the catalyst precursor from step (2) at a temperature in the range of about 50 to 800° C. in the presence of a hydrogen-containing gas to convert the Group VIII metal salt to the Group VIII metal. As an illustration, a catalyst precursor comprising about two weight percent rhodium chloride on a support may be converted to an active catalyst by first, drying the catalyst precursor at a temperature ranging from 100 to 150° C. in air or a gas stream containing oxygen, oxygen fortified air, or oxygen plus inert gaseous components and then, optionally, further heating, or calcining, the precursor at a temperature in the range of 300 to 1000° C. in the presence of a gas consisting of air, oxygen fortified air, or a 0:100 to 100:0 oxygen/inert gas mixture, and then finally heating at a temperature in the range of 50 to 800° C. in the presence of hydrogen/inert gas to convert the rhodium salt to metallic rhodium. Alternatively, the last step involving the reduction of the rhodium salt, or rhodium oxide, to metallic rhodium may be accomplished by using a solution containing a chemical reducing agent, such as sodium formate at temperatures ranging from 25 to 100° C. for 10 to 60 minutes.

A process for the manufacture of BO which comprises contacting EpB and hydrogen in the presence of a catalyst comprising rhodium metal deposited on the catalyst support material of embodiment (1) under hydrogenation conditions of pressure and temperature constitutes the fourth embodiment of the present invention. The hydrogenation of EpB in the presence of a supported rhodium catalyst prepared as described herein results in the selective hydrogenation of the olefinic unsaturation without significant hydrogenolysis of the conjugated epoxy group. As compared to prior art catalysts, the supported rhodium catalysts described herein maintain their catalytic activity in converting EpB to BO over extended periods of operation.

The hydrogenation conditions of temperature and pressure can vary substantially depending on several factors such as contact time with the rhodium catalyst, the amount of catalyst, the amount of rhodium present on the support and the mode of operation. Hydrogenation temperatures of about 20 to 150° C. may be used although milder temperatures in the range of about 25 to 80° C. are advantageous to maximize conversion to the desired BO and minimize conversion to alcohols and aldehydes. The hydrogenation process may be carried out using total pressures in the range of about 0 to 345 bar gauge (barg), preferably about 2 to 56 barg. As noted above, the optimum combination of temperature and pressure depends on other process variables but can be readily ascertained by those skilled in the art. The catalyst utilized in the hydrogenation process preferably comprises a silica support, modified as described herein, containing about 0.25 to 2.0 weight percent rhodium, based on the total weight of the catalyst, deposited thereon.

The hydrogenation process of this invention optionally may be carried out in the presence of an inert, organic solvent. Examples of such solvents include aliphatic and aromatic hydrocarbons such as heptane, cydohexane, toluene, xylene and mixed xylene isomers; alkanols such as ethanol; ethers such as tetrahydrofuran; and the reaction products resulting from the hydrogenation of EpB, e.g., BO, butanol, butyraldehyde or a mixture of any 2 or more thereof. The process may be carried out in a batch, semi-continuous or continuous mode of operation. For example, batch operation may comprise agitating a slurry of a rhodium catalyst in EpB and, optionally, a solvent in a pressure vessel for a time sufficient to convert essentially all of the unsaturated epoxide to other compounds. The catalyst can be separated from the hydrogenated mixture by filtration and the components of the filtrate separated by distillation.

A preferred mode of operation uses a fixed bed of a supported rhodium catalyst wherein EpB is hydrogenated in the gas or, especially, liquid phase, optionally in the presence of an inert diluent or solvent. Liquid phase operation typically involves feeding a solution of EpB in an inert solvent-diluent to the top of a tubular, pressure reactor containing one or more fixed beds of a supported rhodium catalyst. The reactant solution flows (trickles) over the catalyst bed in the presence of hydrogen at elevated temperature and pressure and the hydrogenated product exits the bottom of the reactor and is separated into its components by distillation or extraction. The feed rates employed in liquid phase operation may be in the range of about 0.01 to 100 liquid hour space velocities (LHSV, unit volume of feed per unit volume of catalyst). Under most conditions, the LHSV will be in the range of about 0.1 to 10. Similar reaction conditions may be used when carrying out the process in the gas phase mode. Diluents for the process feed include inert gases as well as hydrogen. The maximum concentration of EpB vapor in the gas feed stream is controlled by the saturation vapor pressure of EpB at the reaction temperature. For a reaction temperature of 50° C., the maximum vapor pressure of EpB is approximately 400 Torr or less partial pressure. The total feed rates for operation as a gas feed, fixed-bed reactor may be in the range of 100 to 20,000 space velocities (gas hourly space velocity—GHSV, unit volume of feed per unit volume of catalyst per hour), more preferably a GHSV in the range of 200 to 20,000.

The process provided by the present invention is further illustrated by the following examples.

PREPARATION OF CATALYSTS

COMPARATIVE CATALYST EXAMPLE 1

A rhodium chloride solution was prepared by diluting 16.39 grams of a concentrated $RhCl_3$ solution, containing 10.98 weight percent Rh, to 400 mL with deionized water. Activated carbon granules, sized 4 by 8 mesh, were added to the diluted rhodium solution. After soaking at room temperature for 30 minutes, the mixture was heated to 85–90° C. and held at that temperature for 20 minutes. Next, 2.5 grams of sodium formate was dissolved in 50 mL of deionized water and the resulting solution was added to the rhodium/carbon mixture. The mixture was held at 85–90° C. for another 15 minutes. Then 4.5 mL of 90 weight percent aqueous formic acid solution, diluted to 30 mL with deionized water, was added to the mixture. The mixture was held at 85–90° C. for an additional 15 minutes to reduce the rhodium to its metallic state and then cooled to room temperature. The resulting catalyst was washed with deionized water until it was free of soluble chloride ions. It then was finished by drying at 110° C. overnight. The finished catalyst contained 1.0 weight percent rhodium.

COMPARATIVE CATALYST EXAMPLE 2

A rhodium chloride solution was prepared by diluting 28.57 grams of a concentrated $RhCl_3$ solution, containing 7.35 weight percent Rh, to 179 mL with deionized water. This solution was sprayed onto 198 grams of 3.2 mm (⅛ inch) diameter silica extrusions in a rotary pan coater. The impregnated extrusions were tumbled and heated by blowing hot air (260° C. nominal temperature) on the glass pan of the rotary coater while slowly tumbling. After an hour of indirect heating, the hot air was again blown directly on the extrusions (480° C. nominal temperature) for 10 minutes. Next, the extrusions were calcined in an oven at 600° C. for 1 hour. The resulting catalyst was washed with deionized water until it was free of soluble chloride ions. It then was finished by drying at 120° C. overnight. The loading of the supported rhodium oxide catalyst was 1.0 weight percent rhodium.

CATALYST EXAMPLE 1

Silica extrusions (3.2 mm diameter; 99 grams) were impregnated with 7.5 grams of 45 weight percent aqueous KOH solution diluted to 69 mL with deionized water, dried at 120° C. overnight, and then calcined at 380° C. A rhodium chloride solution was prepared by diluting 14.29 grams of a concentrated $RhCl_3$ solution, containing 7.35 weight percent Rh, to 79.4 mL with deionized water. The pH of the Rh solution was adjusted to about 1.9 with 7.49 grams of 45 weight percent aqueous KOH solution and then to pH of about 4.6 with 0.09 grams of sodium bicarbonate. This solution was sprayed onto the KOH-impregnated silica extrusions in a rotary pan coater. The impregnated extrusions were tumbled and heated with hot air (260° C. nominal temperature) blowing on them for about 5 minutes. The extrusions then were heated by blowing hot air (260° C. nominal temperature) on the glass pan of the rotary coater while slowly tumbling. After 60 minutes of indirect heating, the extrusions were calcined in an oven at 700° C. for 1 hour. The resulting catalyst was washed with deionized water until it was free of soluble chloride ions. It then was finished by drying at 120° C. overnight. The loading of the supported rhodium oxide catalyst was 1.0 weight percent rhodium.

CATALYST EXAMPLE 2

Silica extrusions (3.2 mm diameter; 74.2 grams) were impregnated with 3.44 grams of magnesium nitrate hexahydrate dissolved in 66.6 mL deionized water, dried at 120° C. for 3 hours, and then calcined at 400° C. for 1 hours. The silica extrusions were next impregnated with 5.63 grams of 45 weight percent aqueous KOH solution diluted to 51.8 mL with deionized water and dried at 120° C. overnight. A rhodium chloride solution was prepared by diluting 8.98 grams of a concentrated $RhCl_3$ solution, containing 10.22 weight percent Rh, to 51.8 mL with deionized water. The pH of the Rh solution was adjusted to about 1.7 with 4.72 grams of 45 weight percent aqueous KOH solution and then to pH of about 4.8 with 0.12 grams of sodium bicarbonate. This solution was sprayed onto the silica extrusions in a rotary pan coater. The impregnated extrusions were tumbled without heat for 15 minutes, and then heated with hot air (260° C. nominal temperature) blowing on them for about 90 minutes. The extrusions were calcined in an oven at 350° C. for 90 minutes, washed with deionized water until it was free of soluble chloride ions, and dried at 120° C. overnight. The catalyst was finished by calcining at 700° C. for 1 hour. The loading of the supported rhodium oxide catalyst was 0.95 weight percent rhodium.

CATALYST EXAMPLE 3

Silica extrusions (3.2 mm diameter; 100 grams) were impregnated with 46 grams of lanthanum trinitrate hexahydrate dissolved in 86 mL deionized water, dried at 125° C. for 4 hours and at 100° C. overnight, and then calcined at 400° C. for 2 hours. Next, 35 grams of this material were impregnated with 2.14 grams of 45 weight percent aqueous KOH solution diluted to 27.3 mL with deionized water and dried at 125° C. overnight. A rhodium chloride solution was prepared by diluting 3.91 grams of a concentrated $RhCl_3$ solution, containing 10.22 weight percent Rh, to 29 mL with deionized water. The pH of the Rh solution was adjusted to about 4.6 with 1.39 grams of 45 weight percent aqueous KOH. This solution was sprayed onto the silica extrusions in a rotary pan coater. The impregnated extrusions were tumbled and heated with hot air to dryness. The extrusions were calcined in an oven at 350° C., washed with deionized water until free of soluble chloride ions, and dried. The catalyst was finished by calcining at 700° C. for 1 hour. The loading of the supported rhodium oxide catalyst was 1.08 weight percent rhodium.

CATALYST EXAMPLE 4

Silica extrusions (3.2 mm diameter; 989.5 grams) were impregnated with 46 grams of magnesium nitrate hexahydrate dissolved in 900 mL deionized water, dried at 120° C. overnight, and then calcined at 400° C. for 1 hour. The silica extrusions were next impregnated with 75 grams of 45 weight percent aqueous KOH solution diluted to 820 mL with deionized water and dried at 120° C. overnight. A rhodium chloride solution was prepared by diluting 72.65 grams of a concentrated RhCl$_3$ solution, containing 10.22 weight percent Rh, to 838 mL with deionized water. The pH of the Rh solution was adjusted to about 1.7 with 36.9 grams of 45 weight percent aqueous KOH solution and then to pH of about 4.7 with 1.35 grams of sodium bicarbonate. This solution was sprayed onto the silica extrusions in a rotary pan coater. The impregnated extrusions were tumbled without heat for 15 minutes, and then heated with hot air (260° C. nominal temperature) blowing on them for about 60 minutes. The extrusions were calcined in an oven at 350° C. for 90 minutes, washed with deionized water until it was free of soluble chloride ions, and dried at 120° C. The catalyst was finished by calcining at 700° C. for 90 minutes. The loading of the supported rhodium oxide catalyst was 0.50 weight percent rhodium.

CATALYST EXAMPLE 5

Silica extrusions (3.2 mm diameter; 993 grams) were impregnated with 46 grams of magnesium nitrate hexahydrate dissolved in 894 mL deionized water, dried at 120° C. overnight, and then calcined at 400° C. for 2 hours. The silica extrusions were next impregnated with 104 grams of 45 weight percent aqueous KOH solution diluted to 894 mL with deionized water and dried at 120° C. overnight. A rhodium chloride solution was prepared by diluting 77.58 grams of a concentrated RhCl$_3$ solution, containing 10.22 weight percent Rh, to 894 mL with deionized water. The pH of the Rh solution was adjusted to about 1.7 with 13 grams of 45 weight percent aqueous KOH solution and then to pH of about 4.9 with 4.62 grams of sodium bicarbonate. This solution was sprayed onto the KOH-impregnated silica extrusions in a rotary pan coater. The impregnated extrusions were tumbled and heated with hot air (260° C. nominal temperature) blowing on them for about 70 minutes. The extrusions were calcined in an oven at 350° C. for 90 minutes, washed with deionized water until it was free of soluble chloride ions, and dried at 120° C. overnight. The catalyst was finished by calcining at 700° C. for 1 hour. The loading of the supported rhodium oxide catalyst was 0.75 weight percent rhodium.

HYDROGENATION OF EPOXYBUTENE

COMPARATIVE HYDROGENATION EXAMPLE 1

This example utilized a 1-liter, high-pressure autoclave with a highspeed Rushton turbine-style impeller. The catalyst was contained in a thimble-shaped, wire mesh basket that was suspended inside the autoclave reactor in a manner that permitted facile transport of reactants and products to and from the catalyst. The feed rate of EpB was controlled precisely by means of high-pressure, dual syringe pumps that permitted long term, continuous operation. Hydrogen gas was introduced from a high-pressure supply via a mass flow controller. Both feeds were introduced directly into the reaction solvent through sintered metal frits in the bottom of the reactor.

The liquid level of the EpB, optional solvent and reaction products in the reactor was controlled by means of a "sip" tube extending downward from the head of the reactor. The total liquid volume of the reactor was approximately 500 mL. Both gas and liquid products exited the reactor through the sip tube and passed through a back pressure-regulating valve that was used to control the pressure, typically 27.6 barg (400 pounds per square inch—psig) total pressure, within the reactor. The liquid product then was cooled and periodically sampled by a remotely-actuated, liquid sampling system. Liquid samples were analyzed by gas chromatography to determine catalyst activity and selectivity. When samples were not being taken, the liquid product was collected in a 3.5 liter product tank. Coarse reactor temperature was controlled by setting the temperature of a 3-zone electrical furnace which surrounded the reactor body to a value approximately 10–20° C. above the desired reaction temperature. Fine temperature control was provided by a time-proportioning temperature controller that periodically opened a solenoid valve to allow filtered water to enter an internal cooling coil.

In the examples, percent conversion of EpB is:

$$\frac{\text{Moles } EpB \text{ Converted to Products}}{\text{Moles } EpB \text{ Fed to the Reactor}} \times 100$$

and percent selectivity to BO is:

$$\frac{\text{Moles } EpB \text{ Converted to } BO}{\text{Moles } EpB \text{ Converted to Products}} \times 100$$

The stirred reactor described above was charged with 5.0 grams of the catalyst of Comparative Catalyst Example 1. The catalyst was pretreated in situ under flowing hydrogen for 2 hours at 100° C. and 27.6 barg (400 psig) hydrogen pressure to reduce any residual rhodium salt to metallic rhodium. A feed mixture comprising 20 weight percent EpB and 80 weight percent cyclohexane was fed to the reactor at a rate of 5 mL per minute while maintaining a reactor temperature of 25° C. and a hydrogen pressure of 27.6 barg. The hydrogenation reaction was operated for 2 hours before EpB feed rate and hydrogen pressure reached stable operating conditions. The results achieved are shown in Table I wherein "Time" is the number of hours of operation prior to sampling the reaction product, "Conversion" is the percent conversion of EpB and "Selectivity" is the percent selectivity to BO.

TABLE I

| Time | Conversion | Selectivity |
|---|---|---|
| 2 | 19.1 | 90.1 |
| 10 | 14.7 | 90.4 |
| 20 | 7.9 | 90.2 |

Table I shows that catalytic activity declined from 19.1% to 7.9% over an 18-hour reaction time, i.e., 58.7% of the catalyst activity was lost after 18 hours of reaction time. The results of analyses of the catalyst both before and after the hydrogenation experiment are shown in Table II wherein Surface Area is given in m$^2$/g for the entire catalyst (Total) and Surface Area attributable to the catalyst micropores (Micropore) and Pore Volume is given in mL/g for the entire catalyst (Total) and for the Pore Volume attributable to the catalyst micropores.

TABLE II

| | Surface Area | | Pore Volume | |
| --- | --- | --- | --- | --- |
| | Total | Micropore | Total | Micropore |
| Before | 1250 | 829 | 0.46 | 0.44 |
| After | 645 | 420 | 0.24 | 0.22 |

In Table II, pore analysis is defined as stated earlier and summarized in Thomas and Thomas, Introduction to the *Principles of Heterogeneous Catalysis*, while surface areas, both total and that due to micropores, is explained more thoroughly in W. J. Moore, *American Scientist*, 48, 109 (1960). The data reported in Table II show that EpB hydrogenation has resulted in substantial loss of micropore volume and micropore surface area. It is believed that the concurrent loss of catalytic activity with loss of micropore accessibility during reaction indicates that Rh contained in the micropores no longer can contribute to the catalytic hydrogenation of EpB to BO.

COMPARATIVE HYDROGENATION EXAMPLE 2

The procedure described in Comparative Hydrogenation Example 1 was repeated using 5.0 grams of the catalyst described in Comparative Catalyst Example 2. After feed rates, reactor volume, and pressure stabilized, catalytic activity was measured. EpB conversion declined from 80.0% to 25.2% over 108 hours of reaction time. Selectivity to BO remained substantially constant at 90.6 to 91.2%. The results of analyses of the catalyst both before and after the hydrogenation experiment are shown in Table III wherein Surface Area is given in $m^2/g$ for the entire catalyst (Total) and Surface Area attributable to the catalyst micropores (Micropore) and Pore Volume is given in mL/g for the entire catalyst (Total) and for the Pore Volume attributable to the catalyst micropores.

TABLE III

| | Surface Area | | Pore Volume | |
| --- | --- | --- | --- | --- |
| | Total | Micropore | Total | Micropore |
| Before | 33.1 | 9.7 | 0.098 | 0.004 |
| After | 17.9 | 2.8 | 0.065 | 0.001 |

The data reported in Table III show that the micropores of the support became blocked to a greater extent than the remainder of the catalyst. Blockage of the micropores leads to a drastic, irreversible loss of catalyst activity.

COMPARATIVE HYDROGENATION EXAMPLE 3

The catalyst employed in Comparative Hydrogenation Example 1 was evaluated in a vapor phase hydrogenation process utilizing a 30 cm long stainless steel, tubular reactor having an inside diameter of 7.6 mm. A catalyst bed consisting of a mixture of 0.1 gram of the catalyst employed in Comparative Hydrogenation Example 1 and 0.3 gram of an inert catalyst support material (to increase the volume of heated catalyst bed) was placed in the tubular reactor and held in place by a plug of glass wool inserted into the tubular reactor. The position of the glass wool plug ensured the catalyst and inert support mixture was positioned in the middle portion of the tubular reactor. Both the catalyst and the support diluent were sieved to give particles ranging in size from 410 to 840 microns (0.0164–0.0331 inches) in diameter. Reaction temperature was maintained at 40° C. by a recirculating water-ethylene glycol bath inside a jacket that enclosed the tubular reactor. This method of temperature control gave well-behaved, isothermal operation. Before reaction, the catalyst was reduced in a stream composed of 20:80 hydrogen:nitrogen mixture at atmosphere pressure for 2 hours at 225° C. Following reduction, the catalyst was cooled to reaction temperature in the same gas flow stream. Nitrogen was then removed from the feed stream and the sample pressurized under flowing hydrogen to a reaction pressure of 6.8 barg.

EpB vapor was added to the hydrogen feed stream by routing the hydrogen flow, or a portion of the hydrogen flow, through a stainless steel, vapor-liquid equilibrium (VLE) saturator maintained at 20° C. and a pressure of 6.8 barg (100 psig) to give a typical composition of 2.12 psi of EpB vapor. The concentration of epoxybutene vapor feed was adjusted by changing the temperature of the VLE and the flow rate of auxiliary (make-up) hydrogen. EpB concentration was typically maintained at 1.8 mole percent in hydrogen. Reaction pressure was maintained at 6.8 barg (100 psig) by means of a back pressure regulator below the reactor but upstream of an in-line gas sample loop. The in-line gas sampling system permitted highly accurate analysis of all reaction products and unreacted EpB. An HP5890 Gas Chromatograph using a Poraplot Q PLOT column attached to a thermal conductivity detector gave quantitative analysis of all reaction products, including n-butanol, n-butyraldehyde, crotonaldehyde, crotyl alcohol, 3-butene-1-ol, and unreacted EpB.

The results achieved are shown in Table IV wherein "Time" is the number of hours of operation prior to the sampling and analysis of the reaction product, "Conversion" is the percent conversion of EpB and "Selectivity" is the percent selectivity to BO.

TABLE IV

| Time | Conversion | Selectivity |
| --- | --- | --- |
| 1 | 29.8 | 81.3 |
| 2 | 23.0 | 91.9 |
| 4 | 16.7 | 90.0 |
| 5 | 15.2 | 89.6 |

Table I shows that catalytic activity declined from 29.8% to 15.2% EpB conversion over an 4-hour reaction time. This substantial loss of activity over this short reaction time is consistent with the results from the stirred, liquid phase feed reactor, indicating micropore plugging again has resulted in short catalyst lifetime.

COMPARATIVE HYDROGENATION EXAMPLE 4

The procedure described in Comparative Hydrogenation Example 3 was repeated using a catalyst bed consisting of a mixture of 0.1 gram of the catalyst employed in Comparative Hydrogenation Example 2 and 0.3 gram of an inert catalyst support material (to increase the volume of heated catalyst bed). Both the catalyst and the support diluent were sieved to give particles ranging in size from 410 to 840 microns (0.0164–0.0331 inches) in diameter. Reaction temperature was maintained at 50° C. by a recirculating water-ethylene glycol bath inside a jacket that enclosed the tubular reactor. Before reaction, the catalyst was reduced in a stream composed of 20:80 hydrogen:nitrogen mixture at atmosphere pressure for 2 hours at 225° C. Following reduction, the catalyst was cooled to reaction temperature in the same gas flow stream. Nitrogen was then removed from the feed stream and the sample pressurized under flowing hydrogen to a reaction pressure of 6.8 barg. The composition of the feed was 2.5 mole percent EpB in hydrogen.

Catalyst activity declined from 90.8% conversion to 55.0% conversion after 69 hours of operation. Selectivity to EpB was constant at 83.3%. The activity was continuing to decline when the experiment was terminated.

HYDROGENATION EXAMPLE 1

The procedure described in Comparative Hydrogenation Example 1 was repeated using 5.0 grams of the catalyst of Catalyst Example 1. A feed mixture comprising 20 weight percent EpB and 80 weight percent cyclohexane was fed to the reactor at a rate of 5 mL per minute while maintaining a reactor temperature of 50° C. and a total pressure of 27.6 barg. Over a reaction period of 180 hours, catalyst activity declined from an EpB conversion rate of 98.4% to an EpB conversion rate of 95.8%.

Selectivity to BO increased from 64.9% to 71.9% over the duration of the experiment. These results indicate that blockage of micropores prior to Rh salt impregnation prevented Rh from being deposited in the micropores of the catalyst which prevented catalyst deactivation by subsequent micropore plugging during the selective hydrogenation of EpB.

HYDROGENATION EXAMPLE 2

The procedure described in Comparative Hydrogenation Example 3 was repeated using a catalyst bed consisting of a mixture of 0.1 gram of the catalyst of Catalyst Example 1 and 0.3 gram of an inert catalyst support material (to increase the volume of heated catalyst bed). Both the catalyst and the support diluent were sieved to give particles ranging in size from 410 to 840 microns (0.0164–0.0331 inches) in diameter.

Reaction temperature was maintained at 50° C. by a recirculating water-ethylene glycol bath inside a jacket that enclosed the tubular reactor. Before reaction, the catalyst was reduced in a stream composed of 20:80 hydrogen:nitrogen mixture at atmosphere pressure for 2 hours at 225° C. Following reduction, the catalyst was cooled to reaction temperature in the same gas flow stream. Nitrogen was then removed from the feed stream and the sample pressurized under flowing hydrogen to a reaction pressure of 6.8 barg. The composition of the feed was 1.3 mole percent EpB in hydrogen. Over a reaction period of 137.5 hours, catalyst activity declined from an EpB conversion rate of 97.7% to an EpB conversion rate of 85.2%. Selectivity to BO increased from 73.7% to 78.4% over the duration of the experiment. The conversion of epoxybutene decreased only 12.5% absolute, or 12.8% of the original activity, indicating that blocking micropores of the silica support had prevented the deposition of catalytic Rh in the micropores of the support material.

HYDROGENATION EXAMPLE 3

The procedure described in Comparative Hydrogenation Example 1 was repeated using 5.0 grams of the catalyst of Catalyst Example 2 consisting of 1 weight percent rhodium deposited on a silica support which had been treated to block the micropores of the silica with magnesium oxide. A feed mixture comprising 20 weight percent EpB and 80 weight percent cyclohexane was fed to the reactor at a rate of 5 mL per minute while maintaining a reactor temperature of 50° C. and a total pressure of 27.6 barg. Over a reaction period of 114 hours, catalyst activity declined from an EpB conversion rate of 98.9% to an EpB conversion rate of 97.5%. The negligible decrease in activity demonstrates that the blockage of the micropores of the silica support materials gives a superior catalyst.

HYDROGENATION EXAMPLE 4

The procedure described in Comparative Hydrogenation Example 3 was repeated using a catalyst bed consisting of a mixture of 0.1 gram of the catalyst of Catalyst Example 2 and 0.3 gram of an inert catalyst support material (to increase the volume of heated catalyst bed). Both the catalyst and the support diluent were sieved to give particles ranging in size from 410 to 840 microns (0.0164–0.0331 inches) in diameter. Reaction temperature was maintained at 40° C. and 50° C. by a recirculating water-ethylene glycol bath inside a jacket that enclosed the tubular reactor. Before reaction, the catalyst was reduced in a stream composed of 20:80 hydrogen:nitrogen mixture at atmosphere pressure for 2 hours at 225° C. Following reduction, the catalyst was cooled to reaction temperature in the same gas flow stream. Nitrogen was then removed from the feed stream and the sample pressurized under flowing hydrogen to a reaction pressure of 6.8 barg. The composition of the feed was 1.4 and 2.0 mole percent EpB in hydrogen. Over a reaction period of 290 hours, EpB conversion rate was 100% at both set of conditions (40° C., 1.4 mole percent EpB in $H_2$; and 50° C., 2.0 mole percent EpB in $H_2$). Selectivities to BO were 88% at 40° C. and 86% at 50° C.

HYDROGENATION EXAMPLE 5

The procedure described in Comparative Hydrogenation Example 3 was repeated using a catalyst bed consisting of a mixture of 0.101 gram of the catalyst of Catalyst Example 3 (consisting of 1 weight percent rhodium deposited on a silica support which had been treated to block the micropores of the silica with lanthanum oxide) and 0.402 gram of an inert silica catalyst support material (to increase the volume of heated catalyst bed). Both the catalyst and the support diluent were sieved to give particles ranging in size from 410 to 840 microns (0.0164–0.0331 inches) in diameter. Reaction temperature was maintained at 40° C. by a recirculating water-ethylene glycol bath inside a jacket that enclosed the tubular reactor. Before reaction, the catalyst was reduced in a stream composed of 20:80 hydrogen:nitrogen mixture at atmosphere pressure for 2 hours at 225° C. Following reduction, the catalyst was cooled to reaction temperature in the same gas flow stream. Nitrogen was then removed from the feed stream and the sample pressurized under flowing hydrogen to a reaction pressure of 6.8 barg. The composition of the feed was 1.4 mole percent EpB in hydrogen. Conversion of EpB under these conditions from 3.0 hours to 66.2 hours of reaction time decreased from 50.4% to 45.0% while selectivity varied from 86.4% to 87.5% EpB over the same time interval. These results, in which conversion decreased only marginally, indicate that $La_2O_3$ had satisfactorily been deposited in and had filled the micropores of the silica support material prior to the deposition of a rhodium salt onto the modified silica support.

HYDROGENATION EXAMPLE 6

The procedure described in Comparative Hydrogenation Example 3 was repeated using a catalyst bed consisting of a mixture of 0.1 gram of the catalyst of Catalyst Example 4

(consisting of 0.5 weight percent rhodium deposited on a silica support which had been treated to block the micropores of the silica with magnesium oxide) and 0.3 gram of an inert silica catalyst support material (to increase the volume of heated catalyst bed). Both the catalyst and the support diluent were sieved to give particles ranging in size from 410 to 840 microns (0.0164–0.0331 inches) in diameter. Varying reaction temperatures were maintained by a recirculating water-ethylene glycol bath inside a jacket that enclosed the tubular reactor. Before reaction, the catalyst was reduced in a stream composed of 20:80 hydrogen:nitrogen mixture at atmosphere pressure for 2 hours at 225° C. Following reduction, the catalyst was cooled to reaction temperature in the same gas flow stream. Nitrogen was then removed from the feed stream and the sample pressurized under flowing hydrogen to a reaction pressure of 6.8 barg. The composition of the feed was varied from 1.3 to 2.1 mole percent EpB in hydrogen. The process conditions and parameters employed and the results achieved are set forth in Table V wherein "Temp" is reactor temperature in ° C, "EpB Conc" is the mole percent concentration of EpB in hydrogen fed to the reactor, "Time Interval" is the period of process operating time, in hours, for a particular combination of conditions/parameters, and "Select" is the percent selectivity to BO. "Contact Time" is the statistical length of time (in seconds) that the reactant gas is in contact with the catalyst particles. Contract time is changed by modifying the gas flow rates of the EpB vapor plus hydrogen feed gases that contact the catalyst. "EpB Conv" is the conversion of EpB fed to the reactor at the reaction conditions/parameters stated for the particular Time Interval indicated. For those Time Intervals for which 2 values are given for EpB Conv, the first value is initial conversion and the second value is the final conversion

TABLE V

| Temp | EpB Conc | Contact Time | Time Interval | Select | EpB Conv |
|---|---|---|---|---|---|
| 41.3 | 1.3 | 0.31 | 3–22 | 87 | 22–19 |
| 51.4 | 1.3 | 0.31 | 23–50 | 85 | 26–22 |
| 51.4 | 2.1 | 0.31 | 51–69 | 85 | 15 |
| 51.4 | 2.1 | 1.21 | 70–72 | 85 | 36 |
| 51.5 | 2.1 | 0.58 | 73–106 | 85 | 25–26 |

The results reported in Table V show that catalyst activity is relatively constant, with only slight decreases in EpB conversion, during the first fifty hours of reaction time. After 50 hours of reaction time, catalyst activity remains constant at the modified reaction conditions. The decrease in catalyst activity from 3–22 hours of reaction time is only 13.7% relative to the initial activity of 22% EpB conversion. The decrease in catalyst activity from 23–50 hours is only 15.3% relative to the initial activity of 26% conversion. These decreases in catalytic activities are far less severe than the performance of Comparison Examples 3 and 4, indicating that MgO has successfully blocked the micropores of the silica support and prevented deposition of the Rh salts during impregnation of Rh component. The constant catalyst activities from 51→69 hours, 70→72 hours, and 73→106 hours of reaction time illustrate that micropore filling by MgO gives long term, stable catalysts that have high selectivity.

HYDROGENATION EXAMPLE 7

The procedure described in Comparative Hydrogenation Example 3 was repeated using a catalyst bed consisting of a mixture of 0.2 gram of the catalyst of Catalyst Example 5 (consisting of 0.75 weight percent rhodium deposited on a silica support which had been treated to block the micropores of the silica with magnesium oxide) and 0.2 gram of an inert silica catalyst support material (to increase the volume of heated catalyst bed). Both the catalyst and the support diluent were sieved to give particles ranging in size from 410 to 840 microns (0.0164–0.0331 inches) in diameter. A reaction temperature of 51° C. was maintained by a recirculating water-ethylene glycol bath inside a jacket that enclosed the tubular reactor. Before reaction, the catalyst was reduced in a stream composed of 20:80 hydrogen:nitrogen mixture at atmosphere pressure for 2 hours at 225° C. Following reduction, the catalyst was cooled to reaction temperature in the same gas flow stream. Nitrogen was then removed from the feed stream and the sample pressurized under flowing hydrogen to a reaction pressure of 6.8 barg. The composition of the feed was 2.1 mole percent EpB in hydrogen. EpB conversion rates after 4.6, 7.6, and 55.9 hours of reaction time were 100.0%, 98.7%, and 97.4%, respectively. Selectivity to BO varied between 65–66%.

The invention has been described in detail with particular reference to preferred embodiments thereof, but it will be understood that variations and modifications can be effected within the spirit and scope of the invention.

We claim:

1. Process for the manufacture of 1,2-epoxybutane (BO) which comprises hydrogenating an 3,4-epoxy-1-butene in the presence of a catalyst comprising rhodium deposited on a catalyst support material selected from the group consisting of aluminum oxides, charcoal, pumice, magnesia, zirconia, kieselguhr, fuller's earth, silicon carbide, porous agglomerates comprising silicon and/or silicon carbide, silica and artificial and natural ceramics containing micropores which constitute less than about 50% of the total surface area of the support material and mesopores and macropores which constitute about 50 to 90% of the total surface area of the support material wherein the micropores are blocked with one or more inorganic oxides.

2. Process according to claim 1 wherein the hydrogenation is carried out at a pressure of about 2 to 56 barg and a temperature of about 25 to 80° C. in the presence of a supported rhodium catalyst comprising 0.01 to 10 weight percent based on the total weight of the catalyst of rhodium deposited on a catalyst support material selected from α-alumina and silica containing micropores blocked with one or more inorganic oxides selected from the group consisting of the oxides of the alkali metals, alkaline earth metals, and lanthanides.

3. Process according to claim 2 wherein the supported rhodium catalyst comprises 0.1 to 5 weight percent based on the total weight of the catalyst of rhodium deposited on a silica catalyst support material containing micropores blocked with one or more inorganic oxides selected from the oxides of the alkaline earth metals.

4. Process for the manufacture of 1,2-epoxybutane (BO) which comprises hydrogenating 3,4-epoxy-1-butene at a pressure of about 2 to 56 barg and a temperature of about 25 to 80° C. in the presence of a supported rhodium catalyst comprising 0.25 to 2.0 weight percent based on the total weight of the catalyst of rhodium deposited on a silica catalyst support material containing micropores which constitute less than about 50% of the total surface area of the support material and mesopores and macropores which constitute about 50 to 90% of the total surface area of the support material wherein the micropores are blocked with one or more alkaline earth metal oxides and the mesopores and macropores are not significantly blocked.

5. Process according to claim 4 wherein the micropores are blocked with magnesium oxide.

* * * * *